United States Patent

Cliffe et al.

[11] Patent Number: 5,610,154
[45] Date of Patent: Mar. 11, 1997

[54] BICYCLIC CARBOXAMIDES

[75] Inventors: Ian A. Cliffe, Farnham Common; Howard L. Mansell, Burnham Bucks; Terence J. Ward, Reading, all of Great Britain; James A. Nelson, Bucks County, Pa.; Uresh S. Shah, Cranbury; Mira A. Kanzelberger, Monmouth Junction, both of N.J.

[73] Assignees: John Wyeth & Brother, Ltd., Maidenhead, England; American Home Products Corp., Madison, N.J.

[21] Appl. No.: 448,962

[22] Filed: May 24, 1995

[30] Foreign Application Priority Data

Sep. 21, 1994 [GB] United Kingdom ............... 9419024

[51] Int. Cl.6 .................... A61K 31/55; C07D 295/16
[52] U.S. Cl. .................... 514/216; 514/253; 514/254; 514/183; 540/583; 544/373; 544/362
[58] Field of Search ............... 540/583; 544/373, 544/362; 514/183, 253, 254, 216

[56] References Cited

FOREIGN PATENT DOCUMENTS

| 481744 | 4/1992 | European Pat. Off. |
| 1129749 | 1/1967 | United Kingdom. |
| 2230781 | 10/1990 | United Kingdom. |
| WO93/11122 | 6/1993 | WIPO. |
| WO94/15919 | 7/1994 | WIPO. |

*Primary Examiner*—Joseph K. McKane
*Assistant Examiner*—Richard S. Myers, Jr.
*Attorney, Agent, or Firm*—Arthur G. Seifert

[57] ABSTRACT

Bicyclic carboxamides of formula I

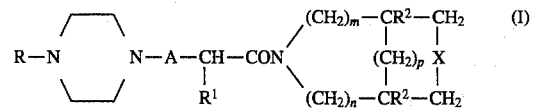

and the pharmaceutically acceptable acid addition salts are $5\text{-}HT_{1A}$ binding agents, particularly $5\text{-}HT_{1A}$ antagonists and may be used, for example, as anxiolytics. In the formula X represents $-CR^2=CR^2-$ or $-(CR^2)_q-$;

m represents 0,1 or 2; n represents 0,1 or 2; p represents 0,1,2 or 3 and q represents 0,1,2 or 3;

A is an alkylene chain of 1 or 2 carbon atoms optionally substituted by one or more lower alkyl groups, R is a mono or bicyclic aryl or heteroaryl radical, $R^1$ is an aryl or aryl(lower)alkyl radical and each $R^2$ is independently hydrogen or lower alkyl.

6 Claims, No Drawings

BICYCLIC CARBOXAMIDES

This invention relates to novel bicyclic carboxamides derivatives, to processes for their preparation, to their use and to pharmaceutical compositions containing them. The novel compounds act on the central nervous system by binding to 5-HT receptors (as more fully explained below) and hence can be used as medicaments for treating humans and other mammals.

The novel compounds of the invention are those of general formula $$R-N\underset{\diagdown\diagup}{\overset{\diagup\diagdown}{N}}-A-CH-CON\underset{R^1}{\diagdown}\underset{(CH_2)_n-CR^2-CH_2}{\overset{(CH_2)_m-CR^2-CH_2}{\diagup}}\underset{|}{(CH_2)_p\ X} \quad (I)$$

and the pharmaceutically acceptable acid addition salts thereof.

In formula I

X represents —CR$^2$=CR$^2$— or —(CR$^2$)q—;

m represents 0,1 or 2; n represents 0, 1 or 2; p represents 0, 1, 2 or 3 and q represents 0, 1, 2 or 3

A is an alkylene chain of 1 or 2 carbon atoms optionally substituted by one or more lower alkyl groups, R is a mono or bicyclic aryl or heteroaryl radical, R$^1$ is an aryl or aryl(lower)alkyl radical and each R$^2$ is independently hydrogen or lower alkyl.

The term "lower" as used herein means that the radical referred to contains 1 to 6 carbon atoms. Preferably such radicals contain 1 to 4 carbon atoms. Examples of "lower alkyl" radicals are methyl, ethyl, propyl, isopropyl, butyl, tert.-butyl, pentyl and isopentyl.

When used herein "aryl" means an aromatic radical having 6 to 10 carbon atoms (e.g. phenyl or naphthyl) which optionally may be substituted by one or more substituents. Preferred substituents are lower alkyl, lower alkenyl, lower alkoxy (e.g. methoxy, ethoxy, propoxy, butoxy), halogen, halo(lower)alkyl (e.g. trifluoromethyl), hydroxy, nitrile, (lower)alkylcarbonyl, (lower)alkoxycarbonyl, amino, (lower)alkylamino, di(lower)alkylamino, aminocarbonyl, (lower)alkylaminocarbonyl, di(lower)alkylaminocarbonyl, nitro, —CHO or thio(lower)alkyl substituents. Two substituents on the aromatic ring may be connected together to form another ring system. For example R may be an optionally substituted tetrahydronaphthyl radical (eg 5-tetralinyl) or a bicyclic oxygen-containing radical of the formula wherein the heterocyclic ring containing the oxygen atom contains a total of 5 to 7 ring members, said heterocyclic ring being non-aromatic and optionally containing one or more hetero ring members (eg O, N or S) in addition to the oxygen atom illustrated and the bicyclic oxygen radical being optionally substituted by one or more substituents such as the substituents mentioned above in connection with "aryl". A preferred example of such a bicyclic oxygen radical is 8-chromanyl or an optionally substituted radical of the formula The term "heteroaryl" refers to an aromatic radical containing one or more hetero atoms (e.g. oxygen, nitrogen, sulphur) and which may be optionally substituted by one or more substituents. Examples of suitable substituents are given above in connection with "aryl" radicals. The heteroaryl radical may, for example, contain up to 12 ring atoms. For example the heteroaryl radical may be a monocyclic radical containing 5 to 7 ring atoms or a bicyclic radical containing 8 to 12 ring atoms. Preferably the hetero ring contains one or two hetero atoms selected from nitrogen, oxygen and sulphur.

When R is a heteroaryl radical it is preferably an optionally substituted pyrimidyl (particularly 2-pyrimidyl), optionally substituted pyridyl (e.g. pyrid-2-yl), optionally substituted indolyl (particularly indol-4-yl and indol-7-yl), optionally substituted pyazinyl (particularly 2-pyrazinyl), optionally substituted quinolinyl or isoquinolinyl (particularly 1-isoquinolinyl) or optionally substituted benzofuran (particularly 4 and 7-benzofuranyl) where the optional substituents are given above in connection with aryl radicals.

Preferred compounds of formula I have the following characteristics either singly or in any possible combination:

(a) the ring system $$-N\underset{\diagdown}{\overset{\diagup}{\phantom{N}}}\underset{(CH_2)_n-CR^2-CH_2}{\overset{(CH_2)_m-CR^2-CH_2}{}}\underset{|}{(CH_2)_p\ X}$$

represents (i)

—N or (ii)

—N or (iii) a radical of formula

—N (CH$_2$)$_p$ (CH$_2$)$_q$ where p is 2 or 3 and q is 0, 1, 2, 3, for example a radical of formula

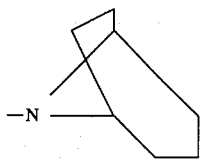

or
(iv)

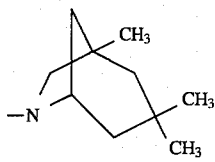

(b) A is —CH$_2$CH$_2$—

(c) R is an optionally substituted phenyl radical e.g. 2-(lower) alkoxyphenyl (for example 2-methoxyphenyl), an optionally substituted pyridyl radical or an optionally substituted indolyl radical (e.g. an optionally substituted indol-4-yl radical) and (d) R$^1$ is substituted or unsubstituted phenyl The compounds of the invention may be prepared by methods known in the art from known starting or starting materials that may be prepared by conventional methods. One method comprises alkylation of a compound of formula

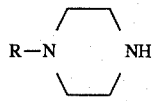 (II)

(where R is as defined above) with an alkylating agent providing the group

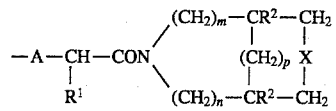 (III)

(where X, m, n, p, A, R$^1$ and R$^2$ have the meanings given above)

The alkylating agent may be, for example a compound of formula

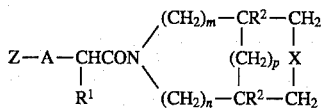 (IV)

where m, n, p, q, A, R$^1$ and R$^2$ are as defined above and Z is a leaving group such as halogen or an alkyl- or arylsulphonyloxy group. Alternatively for preparing compounds where —A— is —CH$_2$— the alkylating agent may be an unsaturated compound of formula

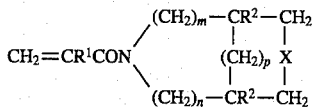 (V)

(where X, m, n, p, R$^1$ and R$^2$ are as defined above) and the compound of formula (V) is reacted with the piperazine of formula (II) by means of a Michael reaction.

The alkylation may also be effected by condensing an aldehyde of formula

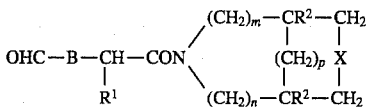

(where X, m, n, p, A and R$^1$ are as defined above and B is a direct bond or a methylene group optionally substituted by one or two lower alkyl groups) with the piperazine of formula (II). The condensation may be carried out with a reducing agent such as sodium triacetoxyborohydride or sodium cyanoborohydride.

In an alternative method of preparing the compound of the invention an amine of formula

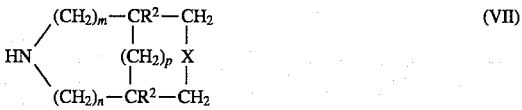 (VII)

(where X, m, n, p and R$^2$ are as defined above) is acylated with an acid of formula

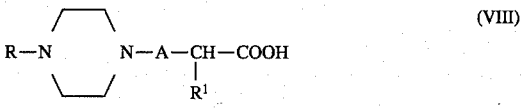 (VIII)

(where A, R and R$^1$ are as defined above) or with an acylating derivative thereof. Examples of acylating derivatives include the acid halides (e.g. acid chlorides), azides, anhydrides, imidazolides (e.g. obtained from carbonyldiimidazole), activated esters or O-acyl ureas obtained from a carbodiimide such as a dialkylcarbodiimide particularly dicyclohexyl-carbodiimide. Preferably the amine is acylated with the acid by the use of a coupling agent such as 1,1'-carbonyldiimidazole, iso-butylchloroformate or diphenylphosphinyl chloride.

The processes described above may be carried out to give a compound of the invention is the form of a free base or as an acid addition salt. If the compound of the invention is obtained as an acid addition salt, the free base can be obtained by basifying a solution of the acid addition salt. Conversely, if the product of the process is a free base an acid addition salt, particularly a pharmaceutically acceptable acid addition salt, may be obtained by dissolving the free base in a suitable organic solvent and treating the solution with an acid, in accordance with conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, lactic, methanesulphonic, malonic, p-toluenesulphonic, oxalic and succinic acids.

The compounds of the invention contain one or more asymmetric carbon atoms, so that the compounds can exist in different steroisomeric forms. All steroisomeric forms are included within the invention. The compounds can be, for example, racemates or optically active forms. The optically active forms can be obtained by resolution of the racemates or by asymmetric synthesis.

The compounds of the present invention possess pharmacological activity. In particular, they act on the central nervous system by binding to 5-HT receptors, particularly receptors of the 5-HT$_{1A}$ type. In general, the compounds selectively bind to receptors of the 5-HT$_{1A}$ type to a much greater extent than they bind to other receptors such as α$_1$. The compounds can be used for the treatment of CNS disorders, such as anxiety in mammals, particularly humans. They may also be useful as antidepressants, antipsychotics (eg for use in schizophrenia, paranoia and manic-depressive illness) hypotensives and as agents for regulating the sleep/wake cycle, feeding behaviour and/or sexual function and as cognition enhancing agents.

The compounds of the invention are tested for 5-$HT_{1A}$ receptor binding activity in rat hippocampal membrane homogenate by the method of B. S. Alexander and M. D. Wood, J. Pharm. Pharmacol., 1988, 40, 888–891. Results for some representative compounds of the invention are given below:

| Compound | 5-$HT_{1A}$ Binding ($IC_{50}$) |
| --- | --- |
| Example 1 | 3.3 nM |
| Example 2 | 1.48 nM |
| Example 5 | 3.73 nM |
| Example 8 | 3.5 nM |
| Example 10 | 17.9 nM |
| Example 14 | 1.96 nM |
| Example 15 | 0.58 nM |
| Example 16 | 4.46 nM |

The invention also provides a pharmaceutical composition comprising a compound of formula (I) or a pharmaceutically acceptable acid addition salt thereof in association with a pharmaceutically acceptable carrier. Any suitable carrier known in the art can be used to prepare the pharmaceutical composition. In such a composition, the carrier is generally a solid or liquid or a mixture of a solid or liquid.

Solid form compositions include powders, granules, tablets, capsules (e.g. hard and soft gelatine capsules), suppositories and pessaries. A solid carrier can be, for example, one or more substances which may also act as flavouring agents, lubricants, solubilisers, suspending agents, fillers, glidants, compression aides, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above, e.g. cellulose derivatives, preferably sodium carboxymethyl cellulose solution), alcohols (e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged composition, for example packeted powders, vials, ampoules, prefilled syringes or sachets containing liquid. The unit dosage form can be, for example, a capsule or tablet itself, or it can be the appropriate number of any such composition in package form. The quantity of the active ingredient in unit dose of composition may be varied or adjusted from 0.5 mg or less to 750 mg or more, according to the particular need and the activity of the active ingredient.

The following Examples illustrate the invention.

EXAMPLE 1

1-(8-Aza-bicyclo[3.2.1]oct-8-yl)-4-[4-(2-methoxyphenyl)-piperazin-1-yl]-2-phenyl-butan-1-one A mixture of 4-[4-(2-methoxyphenyl)piperazin-1-yl]-2-phenylbutanoic acid (4.0 g, 11.3 mmole), desmethyltropane (1.7 g, 15.3 mmole, prepared from tropane by the method used by R. A. Olofson et. al., J. Org. Chem., 1984, 49(11), 2081, for the conversion of O-acetyltropine to O-acetyldesmethyltropine), 1-(3-dimethylaminopropyl)-3-ethylcarbodiimide hydrochloride (2.2 g, 11.3 mmole) and triethylamine (0.19.8 mmole) in methylene chloride (25 mL) was stirred at ambient temperature for 48 hr. The mixture was poured into 1 N sodium hydroxide (100 mL) and extracted with ethyl acetate (3×100 mL). The combined ethyl acetate layer was washed with water (100 mL) and brine (100 mL), dried over anhydrous magnesium sulfate, filtered and concentrated under vacuum to give crude product. Purification of this material by column chromatoghaphy (silica gel with 1% ammonia in ethyl acetate as eluant) followed by the treatment with 1.1 equivalent of 1N hydrogen chloride in ether gave 2.5 g of the title compound as the hydrochloride hemihydrate, m.p. 225°–228° C. (dec.).

Elemental Analysis For: $C_{28}H_{37}N_3O_2 \cdot HCl \cdot 0.5H_2O$ Calcd: C, 68.20; H, 7.97; N, 8.52. Found: C, 68.54; H, 7.72; N, 8.35.

EXAMPLE 2

1-(8-Aza-bicyclo[3.2.1]oct-8-yl)-4-[4-(5-fluoro-2-methoxy-phenyl)-piperazin-1-yl]-2-phenyl-butan-1-one A mixture of the 4-(5-fluoro-2-methoxyphenyl)-piperazine (2.1 g, 10.0 mmole, prepared by method disclosed in U.S. Pat. No. 4,585,773), 1-(8-aza-bicyclo[3.2.1]oct-8-yl)-4-chloro-2-phenyl-butan-1-one (3.40 g, 10.0 mmole), diisopropylethylamine (1.4 g, 11.0 mmole) and potassium iodide (1.66 g, 10.0 mmole) was heated in dimethylformamide (35 mL) to 80° C. for 5 hours. After cooling to ambient temperature, the mixture was poured into water (100 mL) and extracted with ethyl acetate (2×300 mL). The combined ethyl acetate layer was washed with water (100 mL) and brine (100 mL), dried over anhydrous magnesium sulfate, filtered and concentrated under vacuum to give crude product. Purification of this material by column chromatoghaphy (silica gel with 2% methanol in ethyl acetate as eluant) followed by the treatment with 1.1 equivalent of 1N hydrogen chloride in ether gave 1.3 g of the title compound as the hydrochloride quarter hydrate, m.p. 203°–206° C.

Elemental Analysis For: $C_{28}H_{36}FN_3O_2$. HCl . $0.25H_2O$ Calcd: C, 66.39; H, 7.46; N, 8.29. Found: C, 66.18; H, 7.46; N, 8.07.

EXAMPLE 3

(+)-(2S)-1-(8-Aza-bicyclo[3.2.1]oct-8-yl)-4-[4-(5-fluoro-2-methoxy-phenyl)- piperazin-1-yl]-2-phenyl-butan-1-one The title compound was separated from the racemic base, 1-(8-aza-bicyclo[3.2.1]oct-8-yl)-4-[4-(5-fluoro-2-methoxy-phenyl)-piperazin-1-yl]-2-phenyl-butan-1-one (see example 2), by preparative HPLC (Chiralpak, 10 u, 4.6×250 mm, 1:1 ethyl acetate: ethatnol, retention time was 8.865 min) and the resultant enantiomer was treated with 1.1 equivalent of 1 N hydrogen chloride in ether to give 0.097 g of product as the hydrochloride, m.p. 160°–162° C., $[\alpha]_D^{25}$=+14.97 (DMSO).

Elemental Analysis For: $C_{28}H_{36}FN_3O_2$. HCl Calcd: C, 66.98; H, 7.43; N, 8.37. Found: C, 67.09; H, 7.61; N, 8.35.

EXAMPLE 4

(−)-(2R)-1-(8-Aza-bicyclo[3.2.1]oct-8-yl)-4-[4-(5-fluoro-2-methoxy-phenyl)- piperazin-1-yl]-2-phenyl-butan-1-one The title compound was separated from the racemic base, 1-(8-aza-bicyclo[3.2.1]oct-8-yl)-4-[4-(5-fluoro-2-methoxy-phenyl)-piperazin-1-yl]-2-phenyl-butan-1-one (see example 2), by preparative HPLC as described in example 3 (retention time of 9.894 min) and the pure basic enantiomer was treated with 1.1 equivalent of 1 N hydrogen chloride in ether to give 0.170 g of product as the hydrochloride 0.6 hydrate, m.p. 170°–172° C., $[\alpha]_D^{25}$=27.91 (DSMO).

Elemental Analysis For: $C_{28}H_{36}FN_3O_2$. HCl . $0.6 H_2O$ Calcd: C, 65.67; H, 7.51; N, 8.19. Found: C, 65.80; H, 7.95; N, 8.01.

EXAMPLE 5

1-(8-Aza-bicyclo[3.2.1]oct-8-yl)-4-[4-(1H-indol-4-yl)-piperazin- 1-yl]-2-phenyl-butan-1-one The title compound was prepared from 4-(1H-indol-4-yl)-piperazine (1.0 g, 4.97 mmole), 1-(8-aza-bicyclo[3.2.1]oct-8-yl)-4-chloro-2-phenyl-butan-1-one (1.6 g, 4.97 mmole), diisopropylethylamine (0.65 g, 4.97 mmole) and potassium iodide (0.83 g, 4.97 mmole) in dimethylformamide (8 mL) in the manner described in example 2 to yield 0.6 g of product as the hydrochloride 0.75 hydrate, m.p. 150°–170° C.

Elemental Analysis For: $C_{29}H_{36}N_4O$ . HCl . $0.75H_2O$ Calcd: C, 68.76; H, 7.66; N, 11.06. Found: C, 68.59; H, 7.74; N, 11.00.

EXAMPLE 6

(−)-(2R)-1-(8-Aza-bicyclo[3.2.1]oct-8-yl)-4-[4-(1H-indol-4-yl)-piperazin-1-yl]-2-phenyl-butan-1-one The title compound is separated from the racemic base, 1-(8-aza-bicyclo[3.2.1]oct-8-yl)-4-[4-(1H-indol-4-yl)-piperazin-1-yl]-2-phenyl-butan-1-one (see example 5), by preparative HPLC as in example 3 or by chiral synthesis to give the title product as the hydrochloride 1.6 hydrate, m.p. 160°–240° C. (dec.).

Elemental Analysis For: $C_{29}H_{36}N_4O$ . HCl . $1.6H_2O$ Calcd: C, 66.74; H, 7.76; N, 10.73. Found: C, 67.02; H, 7.74; N, 10.33.

EXAMPLE 7

1-(8-Aza-bicyclo[3.2.1]oct-8-yl)-4-[4-(2-methoxy-5-trifluoromethyl- phenyl)-piperazin-1-yl]-2-phenyl-butan-1-one The title compound was prepared from 4-(2-methoxy-5-trifluoromethyl-phenyl)-piperazine 0.7 g, 2.3 mmole, prepared according to the method reported in example 2), 1-(8-aza-bicyclo[3.2.1]oct-8-yl)-4-chloro-2-phenyl-butan-1-one (0.7 g, 2.3 mmole), diisopropylethylamine (0.4 g, 3.0 mmole) and potassium iodide (0.5 g, 3.0 mmole) in dimethylformamide (25 mL) in the manner described in example 2 to yield 0.8 g of title product as the hydrochloride hemihydrate, m.p. 198°–199° C.

Elemental Analysis For: $C_{29}H_{36}F_3N_3O_2$. HCl . $0.5H_2O$ Calcd: C, 62.08; H, 6.83; N, 7.49. Found: C, 62.26; H, 6.56; N, 7.40.

EXAMPLE 8

1-(8-Aza-bicyclo[3.2.1]oct-8-yl)-2-phenyl-4-[4-(pyridin-2-yl)-piperazin-1-yl]-butan-1-one The title compound was prepared from 4-(pyridin-2-yl)-piperazine (1.0 g, 6.0 mmole), 1-(8-aza-bicyclo[3.2.1]oct-8-yl)-4-bromo-2-phenyl-butan-1-one (1.6 g, 4.76 mmole), diisopropylethylamine (0.9 g, 7.0 mmole) and potassium iodide (0.8 g, 5.0 mmole) in dimethylformamide (30 mL) in the manner described in example 2 to yield 1.1 g of product as the dihydrochloride, m.p. 196°–236° C.

Elemental Analysis For: $C_{26}H_{34}N_4O$ . 2HCl Calcd: C, 63.54; H, 7.38; N, 11.40. Found: C, 63.05; H, 7.47; N, 11.31.

EXAMPLE 9

1-(8-Aza-bicyclo[3.2.1]oct-8-yl)-4-[4-(3-methoxy-pyridin-2-yl)-piperazin-1-yl]-2-phenyl-butan-1-one The title compound was prepared from 4-(3-methoxy-pyridin-2-yl)-piperazine (1.0 g, 5.0 mmole) 1-(8-aza-bicyclo[3.2.1]oct-8-yl)-4-bromo-2-phenyl-butan-1-one (1.6 g, 4.76 mmole), diisopropylethylamine (0.9 g, 7.0 mmole) and potassium iodide (0.8 g, 5.0 mmole) in dimethylformamide (30 mL) in the manner described in example 2 to yield 0.87 g of title product as the hydrochloride hydrate, m.p. 140°–147° C.

Elemental Analysis For: $C_{27}H_{36}N_4O_2$. HCl H2O Calcd: C, 64.46; H, 7.81; N, 11.14. Found: C, 64.32; H, 7.91; N, 10.64.

EXAMPLE 10

1-(8-Aza-bicyclo[3.2.1]oct-8-yl)-2-phenyl-4-[4-(3-trifluoromethyl-pyridin-2-yl-piperazin-1-yl]-butan-1-one The title compound was prepared from 4-(3-trifluoromethyl-pyridin-2-yl)-piperazine (0.9 g, 3.9 mmole), 1-(8-azabicyclo[3.2.1]oct-8-yl)-4-chloro-2-phenyl-butan-1-one (1.6 g, 5.50 mmole), diisopropylethylamine (0.7 g, 5.4 mmole) and potassium iodide (0.8 g, 4.8 mmole) in dimethylformamide (30 mL) in the manner described in example 2 to yield 0.98 g of title product as the 1.75 hydrochloride, m.p. 108°–118° C.

Elemental Analysis For: $C_{27}H_{33}N_4O \cdot 1.75$ HCl Calcd: C, 58.92; H, 6.36; N, 10.18. Found: C, 58.87; H, 6.49; N, 10.04.

EXAMPLE 11

1-(8-Aza-bicyclo[3.2.1]oct-8-yl)-2-phenyl-4-[4-(5-trifluoromethyl-pyridin-2-yl)-piperazin-1-yl]-butan-1-one The title compound was prepared from 4-(3-trifluoromethyl-pyridin-2-yl)-piperazine (0.9 g, 3.9 mmole), 1-(8-azabicyclo[3.2.1]oct-8-yl)-4-chloro-2-phenyl-butan-1-one (1.6 g, 5.50 mmole), diisopropylethylamine (0.7 g, 5.4 mmole) and potassium iodide (0.8 g, 4.8 mmole) in dimethylformamide (30 mL) in the manner described in example 2 to yield 0.47 g of title product as the hydrochloride 0.3 hydrate, solid foam, m.p. 85°–120° C., (dec.).

Elemental Analysis For: $C_{27}H_{33}N_4O \cdot HCl \cdot 0.3$ $H_2O$ Calcd: C, 61.37; H, 6.60; N, 10.60. Found: C, 61.50; H, 7.01; N, 10.47.

EXAMPLE 12

4-[4-(2-Methoxy-phenyl)-piperazin-1-yl]-2-phenyl-1(1,3,3-trimethyl-6-aza-bicyclo[3.2.1]oct-6-yl)-butan-1-one A mixture of 4-[4-(2-methoxyphenyl) piperazin-1-yl]-2-phenylbutanoic acid (1.70 g, 5.0 mmole), 1,3,3-trimethyl-6-azabicyclo[3.2.1]-octane (0.77 g, 5.0 mmole), 1-(3-dimethylaminopropyl)-3-ethylcarbodiimide hydrochloride (0.96 g, 5.0 mmole) and triethylamine (0.55 g, 5.0 mmole) in methylene chloride (10 mL) was stirred at ambient temperature for 48 hr. The mixture was poured into 1N sodium hydroxide (75 mL) and extracted with ethyl acetate (3×75 mL). The combined ethyl acetate layer was washed with water (100 mL) and brine (100 mL), dried over anhydrous magnesium sulfate, filtered and concentrated under vacuum to give crude product. This material was treated with 1.1 equivalent of 1N hydrogen chloride in ether (100 mL) to give 1.15 g of the title compound as the hydrochloride sequihydrate, m.p. 110°–145° C. (dec.).

Elemental Analysis For: $C_{31}H_{43}N_3O_2 \cdot HCl \cdot 1.5$ $H_2O$ Calcd: C, 67.31; H, 8.56; N, 7.60. Found: C, 66.94; H, 8.48; N, 7.63.

EXAMPLE 13

1-(3-Aza-bicyclo[3.2.2]non-3-yl)-4-[4-(5-fluoro-2-methoxy-phenyl)-piperazin-1-yl]-2-phenyl-butan-1-one The title compound was prepared from 4-(5-fluoro-2-methoxy-phenyl)-piperazine (2.1 g, 10.0 mmole), 1-(3-azabicyclo[3.2.1]non-3-yl)-4-bromo-2-phenyl-butan-1-one (3.5 g, 10.0 mmole), diisopropylethylamine (1.40 g, 11.0 mmole) and potassium iodide (1.66 g, 10.0 mmole) in dimethylformamide (30 mL) and the purified basic intermediate was treated with 1.1 equivalent of hydrogen chloride in ether to yield 2.5 g of title product as the hydrochloride 1.25 hydrate, m.p. 105°–112° C.

Elemental Analysis For: $C_{29}H_{38}FN_3O_2 \cdot HCl \cdot 1.25$ $H_2O$ Calcd: C, 64.67; H, 7.77; N, 7.80. Found: C, 64.74; H, 7.66; N, 7.56.

EXAMPLE 14

1-(3-Aza-bicyclo[3.2.2]non-3-yl)-4-[4-(1H-indol-4-yl)-piperazin-1-yl]-2-phenylbutan-1-one A mixture of 4-piperazinoindole (1.03 g, 5.1 mmole) 1-(3-azabicyclo[3.2.2]non-3-yl)-4-chloro-2-phenyl-butan-1-one (1.44 g, 4.7 mmole) and diisopropylethylamine (0.66 g, 0.89 mL, 5.1 mmole) in anhydrous dimethylformamide (50 mL) were stirred and heated at 80° C. for 1 h. The dimethylformamide was removed under reduced pressure and the brown residue dissolved dilute hydrochloric acid, washed with ether, basified with potassium carbonate solution and the oil extracted into dichloromethane, dried (MgSO4) and evaporated under reduced pressure to give a brown oil. The oil was purified by chromatography on alumina (30% ethylacetate in hexane) to yield 1.3 g of oil. Solution of the oil in ethylacetate and addition of an ethereal solution of hydrogen chloride precipitated of the title compound, as the hydrochloride salt 1.25 g, mp 175°–179.5° C.

Elemental Analysis for: $C_{30}H_{38}N_4O \cdot 2HCl \cdot H_2O$ Found: C, 64.4; H, 7.4; N, 9.9% Calc: C, 64.1; H, 7.54; N, 10.0%

EXAMPLE 15

1-(3-Azabicyclo[3.2.2]non-3-yl)-4-[4-(2-methoxyphenyl)piperazin-1-yl]-2-phenyl]-butan-1-one A mixture of 4-[4-(2-methoxyphenyl)piperazin-1-yl]-2-phenyl butanoic acid (1.77 g, 5.0 mmole), dicyclohexylcarbodiimide (1.03 g, 5.0 mmol), 3-azabicyclo[3.2.2]nonane hydrochloride (808 mg, 5.0 mmol) and triethylamine (0.75 mL, 0.55 g, 5.4 mmol) in dichloromethane were stirred at ambient temperature for 18 h. The reaction mixture was filtered and the precipitate washed with dichloromethane (2×10 mL). Concentration under reduced pressure gave a yellow foam which was chromatographed on silica, using ethyl acetate as eluant to give a colourless gum (1.83 g). The dihydrochloride was obtained by precipitation from an ethylacetate solution with a solution of ethereal hydrogen chloride affording 1.62 g mp 194°–198° C.

Elemental Analysis for: $C_{29}H_{39}N_3O_2 \cdot 2HCl \cdot 0.5H_2O$ Found: C, 64.0; H, 7.9; N, 7.9% Calc: C, 64.1; H, 7.8; N, 7.7%

EXAMPLE 16

(a) 1-(1,3,3a,4,7,7a-Hexahydro-isoindol-2-yl)-4-chloro-2-phenyl-butan-1-one.

4-Bromo-2-phenylbutanoic acid (4.86 g 0.02 mol), dimethyl formamide (0.5 mL), and thionyl chloride (2.2 mL 0.03 mol) were refluxed in dichloromethane (50 mL) for 2.5 hours under nitrogen. The reaction was evaporated. The residue was evaporated three times with benzene and then dissolved in diethyl ether (50 mL). The solution was chilled in ice and diisopropyl ethylamine (2.6 g 0.02 mol) and 1,3,3a,4,7,7a-hexahydroindole (2.46 g, 0.02 mol) were added. After 2 hours the reaction was essentially complete (TLC uniplate/EtAc). One half of the solution was washed with 10% citric acid, saturated NaHCO$_3$, brine, and dried over Na$_2$SO$_4$. The solution was evaporated. Yield 2.7 g 89%. The oil was chromatographed on dry column silica gel (100 mL) and eluted with ethyl acetate. Yield 2.4 g (68.9%).

(b) 1-(1,3,3a,4,7,7a-Hexahydroisoindol-2-yl)-4-[4-(2-methoxyphenyl)piperazin-1-yl]-2-phenylbutan-1-one, One half of the ether solution of the chloroamide product of Example 16(a) (0.01 mol) was diluted with DMF(75 mL), the ether was evaporated and 2-methoxyphenylpiperazine (1.93 g, 0.01 mol) and diisopropyl ethyl amine (1.75 mL, 0.01 mol) were added. The mixture was stirred 72 hours at room temperature. Water (75 mL) was added and the solution was extracted with ethyl acetate (4×75 mL). The ethyl acetate was washed with saturated NaHCO$_3$, brine, and dried (Na$_2$SO$_4$). Yield 4.4 g (95.7%). The product was purified by chromatography on dry column silica (400 mL) eluted with ethyl acetate. Yield 2.5 g. The amine was dissolved in diethyl ether (100 mL) and acidified with 3.6N HCl in ethyl acetate (4.0 mL). The dihydrochloride was filtered, washed with ether, and dried in vacuo at room temperature to give the title product as the dihydrochloride hemihydrate. Yield 1.85 g., m.p. 209°–211° C.

Elemental Analysis for: C$_{29}$H$_{37}$N$_3$O$_2$.2HCl.1/2H$_2$O Calc'd: C, 64.32; H, 7.45; N, 7.76 Found: C, 64.04; H, 7.40; N, 7.44

EXAMPLE 17

(a) 1-(Octahydro-isoindol-2-yl)-4-bromo-2-phenyl-butan-1-one

4-Bromo-2-phenylbutanoic acid (4.86 g, 0.02 mol) and thionyl chloride (2.2 mL, 0.03 mol) were refluxed in dichloromethane (100 mL) under nitrogen for 3 hours. The solution was evaporated and flushed with benzene three times. The residue was dissolved in diethyl ether (50 mL) and cooled in an ice bath. Octahydroisoindole (2.5 g, 0.02 mol) and diisopropylethylamine (3.5 mL, 0.02 mol) dissolved in diethyl ether (50 mL) were added and the reaction was stirred for 60 hours at room temperature. TLC (Uniplate/ EtOAc) showed essentially complete reaction. The solution was washed with water, sat. NaHCO$_3$, and dried (Na$_2$SO$_4$). Evaporation of solvent left crude product. Yield 6.46 g.

(b) 4-[4-(2-Methoxyphenyl)piperazin-1-yl]-1-(octahydroisoindol-2-yl)-2-phenylbutan-1-one 1-(Octahydro-isoindol-2-yl)-4-bromo-2-phenyl-butan-1-one (3.23 g, 0.0092 mol), diisopropylethylamine (1.75 mL, 0.01 mol) and 2-methoxyphenylpiperazine (1.93 g, 0.01 mol) were stirred in DMF (50 mL) for 48 hours at room temperature. Water (100 mL) was added and the solution was extracted with ethyl acetate (4×50 mL). The ethyl acetate solution was washed with brine and dried (Na$_2$SO$_4$). The crude product was purified by chromatography on a 200 mL silica dry column. Elution with ethyl acetate-hexane (1:1) removed the less polar impurities. The product was eluted with ethyl acetate. Yield 1.8 g, (39%). The gum was dissolved in acetone (50 mL), acidified with 3.7N HCl in ethyl acetate, and precipitated by the addition of diethyl ether (100 mL) to give the title compound as the dihydrochloride hydrate. Yield 1.4 g (25%); m.p. 190°–193° C.

Elemental Analysis for: C$_{29}$H$_{39}$N$_3$O$_2$.2HCl. H$_2$O Calc'd: C, 63.04; H, 7.84; N, 7.60 Found: C, 63.01; H, 7.76; N, 7.48

EXAMPLE 18

(+)-(2S)-1-(8-Aza-bicyclo[3.2.1]oct-8-yl)-4-[4-(1H-indol-4-yl)-piperazin-1-yl]-2-phenyl-butan-1-one The title compound is separated from the racemic base, 1-(8-aza-bicyclo[3.2.1]oct-8-yl)-4-[4-(1H-indol-4-yl)-piperazin-1-yl]-2-phenyl-butan-1-one (see example 5), by preparative HPLC as in example 3 or by chiral synthesis to give the title product as the hydrochloride hemihydrate, m.p. 227°–230° C. (dec.).

Elemental Analysis For: C$_{29}$H$_{36}$N$_4$O. HCl. 0.5 H$_2$O Calcd: C, 69.37; H, 7.63; N, 11.16. Found: C, 69.44; H, 7.68; N, 11.09.

We claim:

1. A compound of formula I $$R-N\underset{\diagdown}{\diagup}N-A-\underset{R^1}{\underset{|}{CH}}-CON\diagup^{(CH_2)_m-CR^2-CH_2}_{\diagdown(CH_2)_n-CR^2-CH_2}\overset{(CH_2)_p}{|}X \quad (I)$$

or a pharmaceutically acceptable salt thereof in which

X represents —CR$^2$=CR$^2$— or —(CR$^2$)$_q$;

m represents 0, 1 or 2; n represents 0, 1 or 2; p represents 0, 1, 2 or 3 and q represents 0, 1, 2 or 3

A is an alkylene chain of 1 or 2 carbon atoms optionally substituted by one or more lower alkyl groups, R is a mono or bicyclic aryl or heteroaryl radical, wherein aryl is a phenyl, naphthyl or tetrahydronaphthyl radical optionally substituted by one or more substituents selected from C$_{1-6}$-alkyl, C$_{1-6}$ alkenyl, C$_{1-6}$ alkynyl, C$_{1-6}$alkoxy, halogen, halo(C$_{1-6}$)alkyl (e.g. trifluoromethyl), hydroxy, nitrile, (C$_{1-6}$)alkylcarbonyl, (C$_{1-6}$)alkoxy-carbonyl, amino, (C$_{1-6}$)alkylamino, di(C$_{1-6}$)alkylamino, aminocarbonyl, (C$_{1-6}$)alkylaminocarbonyl, di(C$_{1-6}$)alkylaminocarbonyl, nitro, —CHO or thio(C$_{1-6}$)alkyl; or a bicyclic oxygen-containing radical of the formula wherein the heterocyclic ring containing the oxygen atom contains a total of 5 to 7 ring atoms, is non-aromatic, optionally contains one further oxygen atom, and may be optionally substituted as above; and heteroaryl is an aromatic radical selected from a monocyclic heteroaryl radical containing 5 to 7 ring atoms or a bicyclic heteroaryl radical containing 8 to 10 ring atoms, one or two hetero ring atoms being selected from nitrogen, oxygen and sulphur, which radical may be optionally substituted as above for aryl;

R$^1$ is an aryl or aryl(lower)alkyl radical, and each R$^2$ is independently hydrogen or lower alkyl.

2. A compound as claimed in claim 1 wherein $$-N\diagup^{(CH_2)_m-CR^2-CH_2}_{\diagdown(CH_2)_n-CR^2-CH_2}\overset{(CH_2)_p}{|}X$$

represents (i)

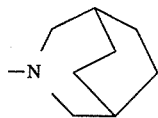

or (ii)

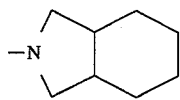

or (iii) a radical of formula

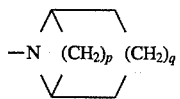

where p is 2 or 3 and q is 0, 1, 2, 3 or (iv)

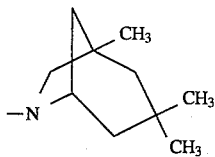

3. A compound as claimed in claim 1 wherein A is —$CH_2CH_2$—.

4. A compound as claimed in claim 1 wherein R is 2-(lower-alkoxy)phenyl, pyridyl, or indolyl.

5. A compound as claimed in claim 1 which is 1-(8-aza-bicyclo[3.2.1]oct-8-yl)-4-[4-(2-methoxy-phenyl)-piperazin-1-yl]-2-phenylbutan-1-one or 1-(8-aza-bicyclo[3.2.1]oct-8-yl)-4-[4-(5-fluoro-2-methoxy-phenyl)-piperazin-1-yl]-2-phenyl-butan-1-one or 1-(8-aza-bicyclo[3.2.1]oct-8-yl)-4-[4-(1H-indol-4-yl)-piperazin-1-yl]-2-phenyl-butan-1-one or 1-(8-aza-bicyclo[3.2.1]oct-8-yl)-4-[4-(2-methoxy-5-trifluoromethyl-phenyl)-piperazin-1-yl]-2-phenyl-butan-1-one or 1-(8-aza-bicyclo[3.2.1]oct-8-yl)-2-phenyl-4-[4-(pyridin-2-yl)-piperazin-1-yl]-butan-1-one or 1-(8-aza-bicyclo[3.2.1]oct-8-yl)-4-[4-(3-methoxy-pyridin-2-yl)-piperazin-1-yl]-2-phenyl-butan-1-one or 1-(8-aza-bicyclo[3.2.1]oct-8-yl)-2-phenyl-4-[4-(3-trifluoromethyl-pyridin-2-yl)piperazin-1-yl]-butan-1-one or 1-(8-aza-bicyclo[3.2.1]oct-8-yl)-2-phenyl-4-[4-(5-trifluoromethyl-pyridin-2-yl)piperazin-1-yl]-butan-1-one or 4-[4-(2-methoxy-phenyl)-piperazin-1-yl]-2-phenyl-1(1,3,3-trimethyl-6-aza-bicyclo[3.2.1]oct-6-yl)-butan-1-one or 1-(3-aza-bicyclo[3.2.2]non-3-yl)-4-]4-(5-fluoro-2-methoxy-phenyl)-piperazin-1-yl]-2-phenyl-butan-1-one or 1-(3-aza-bicyclo[3.2.2]non-3-yl)-4-[4-(1H-indol-4-yl)-piperazin-1-yl]-2-phenylbutan-1-one or 1-(3-azabicyclo[3.2.2]non-3-yl)-4-[4-(2-methoxyphenyl)piperazin-1-yl]-2-phenyl]butan-1-one or 1-(1,3,3a,4,7,7a-hexahydroisoindol-2-yl)-4-4-(2-methoxyphenyl)piperazin-1-yl]-2-phenylbutan-1-one or 4-[4-(2-methoxyphenyl)piperazin-1-yl]-1-(octahydroisoindol-2-yl)-2-phenylbutan-1-one or a pharmaceutically acceptable salt thereof.

6. A method of treating anxiety in a mammal which comprises administering to said mammal an effective amount of a compound claimed in claim 1.

* * * * *